(12) United States Patent
Lin

(10) Patent No.: US 10,532,210 B2
(45) Date of Patent: Jan. 14, 2020

(54) DEVICE FOR STIMULATING OPTIC NERVE FIBERS

(71) Applicant: Po-Kang Lin, Taipei (TW)

(72) Inventor: Po-Kang Lin, Taipei (TW)

( * ) Notice: Subject to any disclaimer, the term of this patent is extended or adjusted under 35 U.S.C. 154(b) by 93 days.

(21) Appl. No.: 15/590,076

(22) Filed: May 9, 2017

(65) Prior Publication Data

US 2018/0326214 A1    Nov. 15, 2018

(51) Int. Cl.
*A61N 1/36* (2006.01)
*A61N 1/05* (2006.01)

(52) U.S. Cl.
CPC ....... *A61N 1/36046* (2013.01); *A61N 1/0526* (2013.01); *A61N 1/0543* (2013.01)

(58) Field of Classification Search
CPC .................................................. A61N 1/36046
See application file for complete search history.

(56) References Cited

U.S. PATENT DOCUMENTS

| | | | |
|---|---|---|---|
| 6,185,463 B1* | 2/2001 | Baudino | A61N 1/05 607/119 |
| 7,257,446 B2* | 8/2007 | Greenberg | A61N 1/36046 607/54 |
| 9,333,361 B2* | 5/2016 | Li | A61N 1/36182 |
| 2007/0191910 A1* | 8/2007 | Ren | A61N 1/36046 607/54 |
| 2012/0035725 A1* | 2/2012 | Gefen | A61N 1/36046 623/6.22 |
| 2016/0121130 A1* | 5/2016 | Cinbis | A61N 1/3621 607/4 |
| 2016/0213926 A1* | 7/2016 | Fukuma | A61N 1/36046 |

* cited by examiner

*Primary Examiner* — William J Levicky
(74) *Attorney, Agent, or Firm* — Lin & Associates Intellectual Property, Inc.

(57) ABSTRACT

The present invention provides a device for stimulating optic nerve fibers. The device includes a plurality of columnar electrodes and a power source. The columnar electrodes are disposed respectively in parallel to a length direction of an optic nerve of a human eye and are also disposed around the optic nerve along a circumferential direction thereof. Each of the columnar electrodes has a length. The power source is configured to supply power to the columnar electrodes. A human retina consists of the optic nerve fibers, which are connected to the optic nerve and a macular area of the human eye in a form of layers. The columnar electrodes are configured to stimulate the optic nerve fibers around the optic nerve with electrical stimulation.

20 Claims, 18 Drawing Sheets

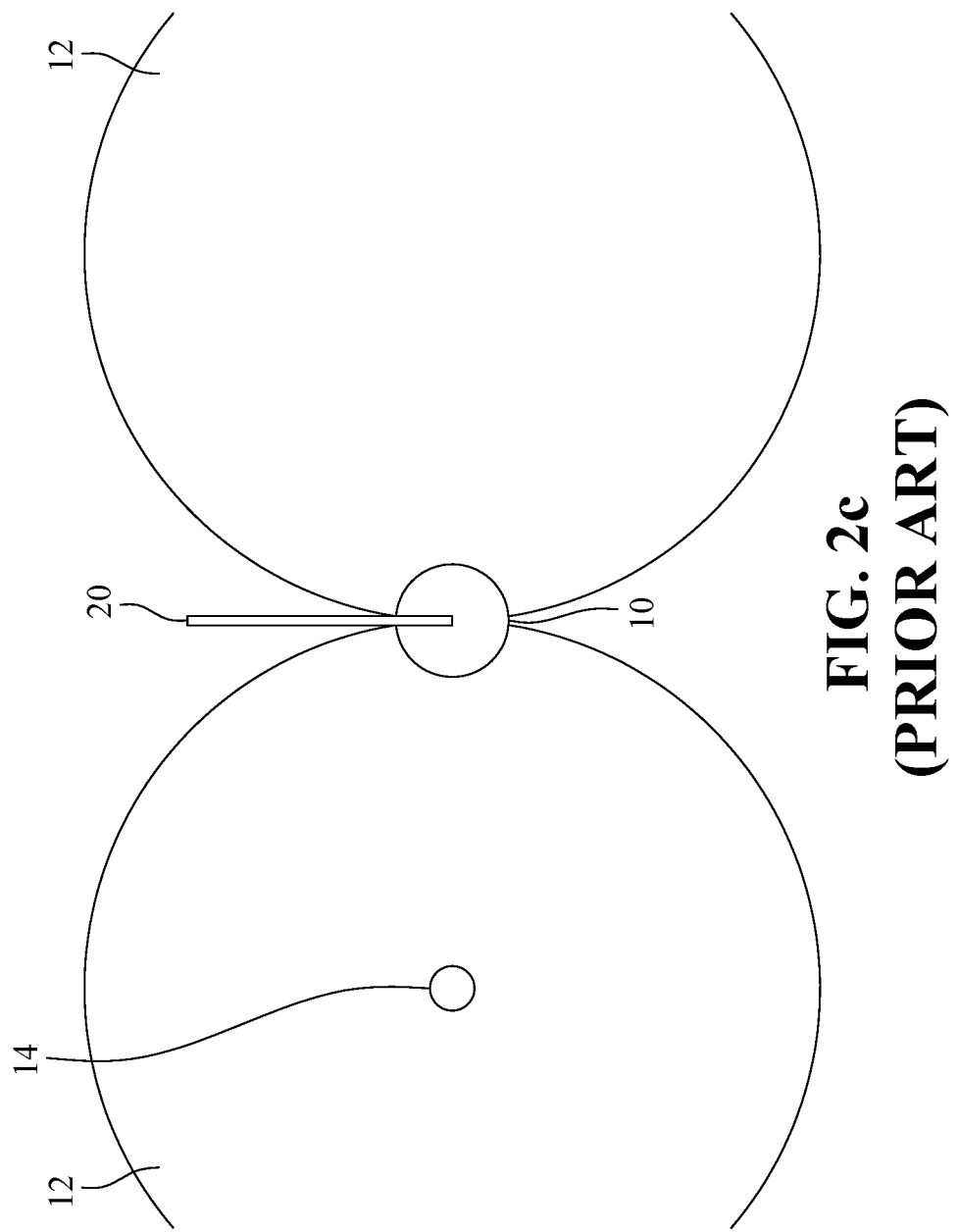

DEVICE FOR STIMULATING OPTIC NERVE FIBERS

BACKGROUND OF THE INVENTION

1. Field of the Invention

The present invention relates to a nerve stimulating device, more particularly, relates to a device for stimulating optic nerve fibers with electrodes.

2. The Prior Arts

According to the statistics of World Health Organization (WHO), population that suffers from eye diseases has exceeded 45 million, and such population is estimated to increase to 76 million in the year of 2020. Amongst all kinds of eye diseases, if optic nerves or the retina of a human eye suffers from certain diseases or is damaged, the vision of the human eye may be compromised, as well as its perception to colors of the outside world.

FIG. 1 is a schematic view illustrating certain structures of a human eye. It should be noted that only the structure of ocular fundus is illustrated. As shown in FIG. 1, the ocular fundus of the human eye 1 includes an optic nerve 10 and a retina 12. The optic nerve 10 and retina 12 are connected by optic nerve fibers (not shown in FIG. 1) in a macular area 14. The optic nerve 10 is capable of transmitting images to the brain, and it includes a protection layer 101 at an outer portion thereof. The retina 12 is located at an innermost layer of the human eye 1, and it is filled with photoreceptor cells and optic nerve fibers. Blood is supplied to the retina via choroid and omentum arteries. The macular area 14 is located at the center of the retina 12. The center of the macular area 14 is a recessed portion, which is also known as the central fovea. It should be noted that the human eye 1 shown in FIG. 1 is a right eye.

When a retina or an optic nerve is damaged or suffers from diseases that prevent them from functioning properly, one often relies on external forces to stimulate the retina or optic nerve; alternatively, an artificial retina may be directly planted into a human eye. In such a way, the problems caused by damages in or diseases of the retina or optic nerve may be resolved, and the retina or optic nerve may once again function properly. A few conventional methods for resolving such problems will be described in the following sections.

FIG. 2a is a section view illustrating a structure of a first conventional implementation. FIG. 2a is a view viewed from an x-direction (i.e. a front side of the ocular fundus inside the human eye 1) indicated in FIG. 1. As shown in FIG. 2, a retina chip 16 is disposed in the macular area 14 of the retina 12 in the first conventional implementation. The retina chip 16 may be used to simulate photoreceptor cells of the retina 12, thereby allowing the human eye 1 to function properly via the retina chip 16. However, the complexity in structure of such an implementation will cause an increase in the manufacturing cost; in addition, an image simulated by the retina chip 16 has a rather low resolution.

FIG. 2b is a schematic view illustrating a structure of a second conventional implementation. As shown in FIG. 2b, an electrode wire 18 is wrapped around the protection layer 101 of the optic nerve 10 in the second conventional implementation. The electrode wire 18 in such an implementation is configured to stimulate the optic nerve 10 through electrical stimulation, thereby allowing the optic nerve 10 to function properly again. However, because of the protection layer 101 outside the optic nerve 10, the electricity induced needs to penetrate through the protection layer 101 first before it can reach the optic nerve 10. Therefore, the electrical stimulation of the second conventional implementation has limited effects.

FIG. 2c is a schematic view illustrating a structure of a third conventional implementation. As shown in FIG. 2c, an electrode pin 20 is inserted into the optic nerve 10 in the third conventional implementation. The electrode pin 20 in such an implementation is configured to stimulate the optic nerve 10 through electrical stimulation, thereby allowing the optic nerve 10 to function properly again. However, it is quite dangerous to insert the electrode pin 20 into the optic nerve 10, thereby rendering the whole implementation process difficult.

Based on the above reasons, in the regard of repairing retina or optic nerve damages, there is a need to develop a new stimulation device with a simple structure, effective stimulation effects and a less dangerous implementation method.

SUMMARY OF THE INVENTION

A primary objective of the present invention is to provide a device for stimulating optic nerve fibers. The device includes a plurality of columnar electrodes and a power source. The columnar electrodes are respectively disposed in parallel to a length direction of an optic nerve of a human eye, and are also disposed around the optic nerve along a circumferential direction thereof. Each of the columnar electrodes has a length. The power source is configured to supply power to the columnar electrodes. A human retina consists of the optic nerve fibers, which are connected to the optic nerve and a macular area of the human eye in a form of layers. The columnar electrodes are configured to stimulate the optic nerve fibers around the optic nerve with electrical stimulation.

Preferably, each of the columnar electrodes comprises a plurality of lateral electrodes. Each of the lateral electrodes is configured to stimulate a different layer of the optic nerve fibers amongst multiple layers of the optic nerve fibers with electrical stimulation.

Preferably, the lateral electrodes are evenly distributed on each of the columnar electrodes based on the length thereof.

Preferably, the columnar electrodes are located between the optic nerve and the macular area, and are arranged in a rectangular array or a fan-shaped array.

Preferably, each of the columnar electrodes comprises a plurality of recessed portions. Each of the recessed portions comprises an insulation layer, and each of the lateral electrodes is embedded into each of the recessed portions having the insulation layer.

Preferably, each of the lateral electrodes is attached to an insulation layer, and each of the insulation layers with the lateral electrode is attached to one of the columnar electrodes.

Preferably, the lengths of the columnar electrodes are the same as or different from each other.

Preferably, when the lengths of the columnar electrodes are different, each of the lengths of the columnar electrodes is adjusted according to a curvature of the optic nerve fibers.

Preferably, a sensor and a controller, which are disposed inside the human eye, are electrically connected to the columnar electrodes. When light from an external light source enters the sensor, a signal is sent to the controller from the sensor, thereby controlling the columnar electrodes to perform electrical stimulation via the controller.

Preferably, a sensor and a controller, which are electrically connected with each other, are further disposed on each of the columnar electrodes. The sensor is configured to detect whether a visual signal has been transmitted by the optic nerve. When the sensor detects that the optic signal has been transmitted, a signal is sent to the controller from the sensor, thereby controlling the columnar electrodes to perform electrical stimulation via the controller.

Preferably, a photo-electrical conversion module, which is electrically connected to the columnar electrodes, is further disposed in the human eye. When light from an external light source enters the human eye, the photo-electrical conversion module converts light energy of the external light into electrical energy and further supplies the electrical energy to the columnar electrodes, thereby allowing the columnar electrodes to perform electrical stimulation.

Preferably, the power source is disposed inside each of the columnar electrodes, inside a human body or outside of the human body.

Preferably, the power source is a solar powered power source.

Other purposes, advantages and innovative features of the present invention will become apparent to those skilled in the art after reading the following examples with reference to the appended drawings.

BRIEF DESCRIPTION OF THE DRAWINGS

The above description and summary of the present invention can be better understood by reading the following examples with reference to the appended drawings. For the purposes of explanation of the present invention, preferred embodiments are illustrated in the figures. It should be understood that the present invention is not limited to the specific arrangement and configuration of the devices shown in the figures.

FIG. 2c is a schematic view illustrating a structure of a third conventional implementation;

DETAILED DESCRIPTION OF THE PREFERRED EMBODIMENT

The accompanying drawings are included to provide a further understanding of the invention, and are incorporated in and constitute a part of this specification. Similar or identical elements are given the same reference numbers. Please be noted that the figures of the present invention are provided in a simplified form and are not drawn to scale.

Figure 1:
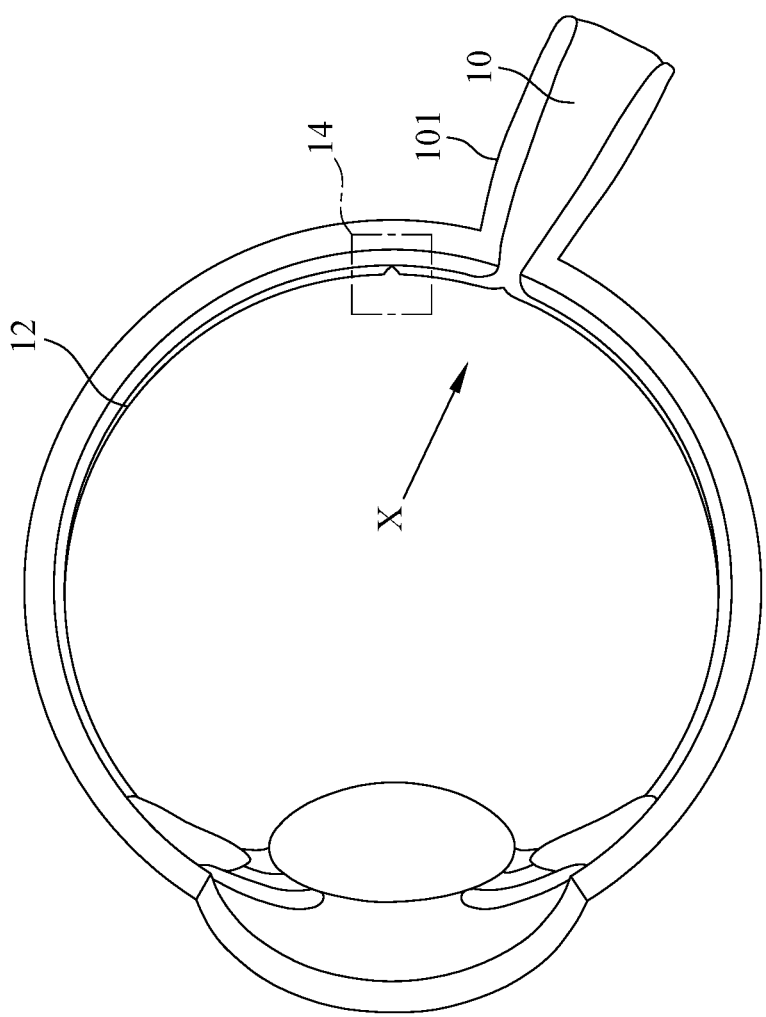
FIG. 1 is a schematic view illustrating a structure of an eye.
Figure 2A:
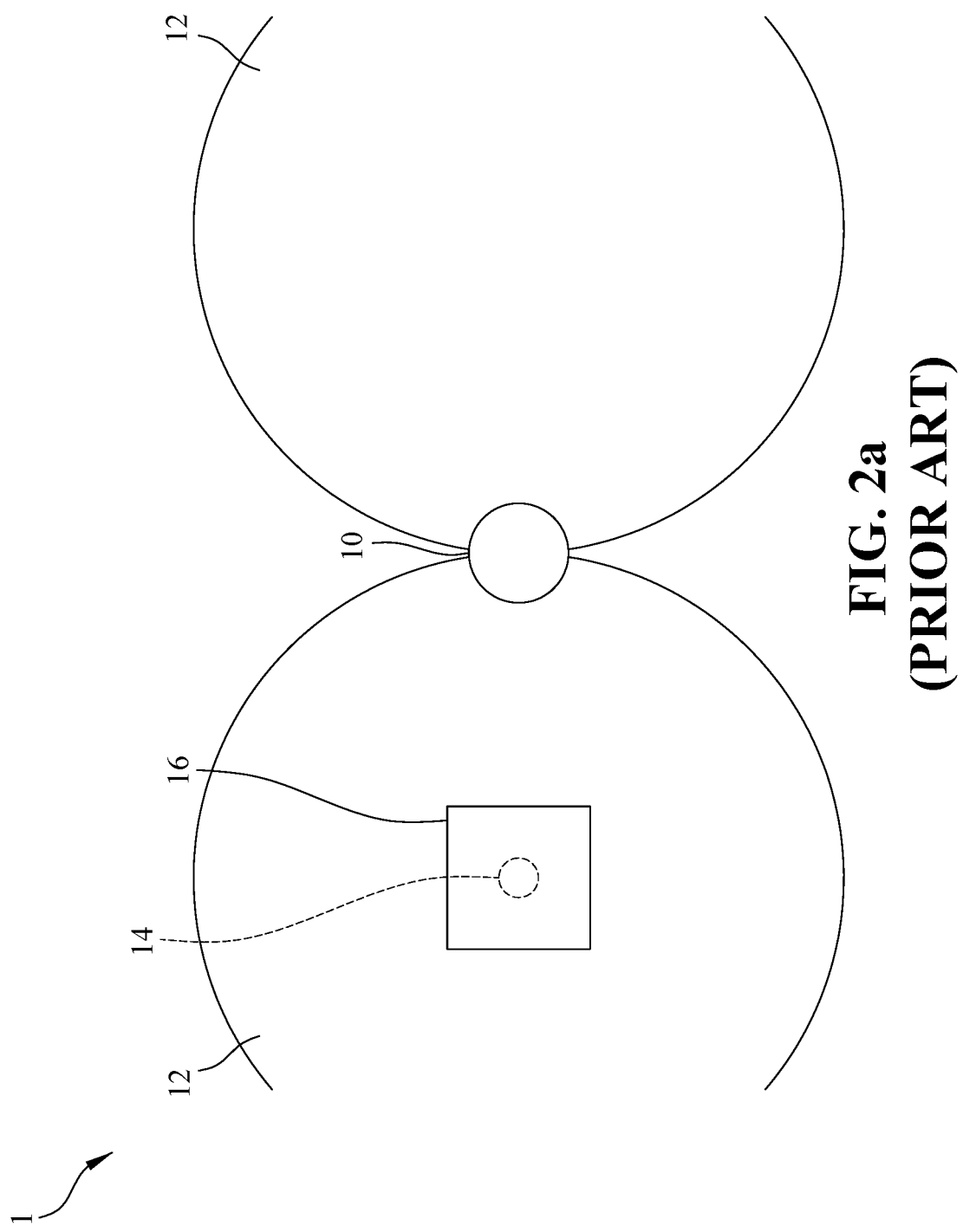
FIG. 2a is a section view illustrating a structure of a first conventional implementation.
Figure 2B:
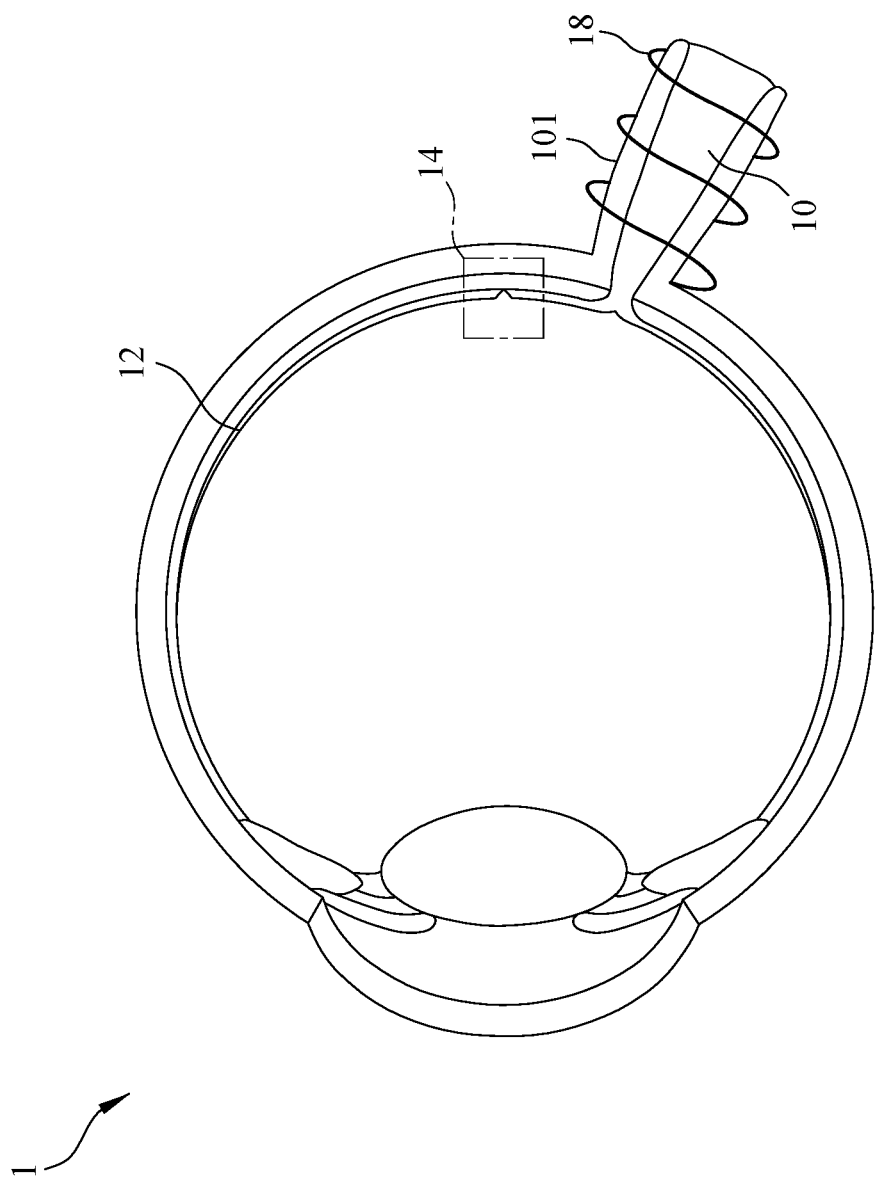
FIG. 2b is a schematic view illustrating a structure of a second conventional implementation.
Figure 3A:
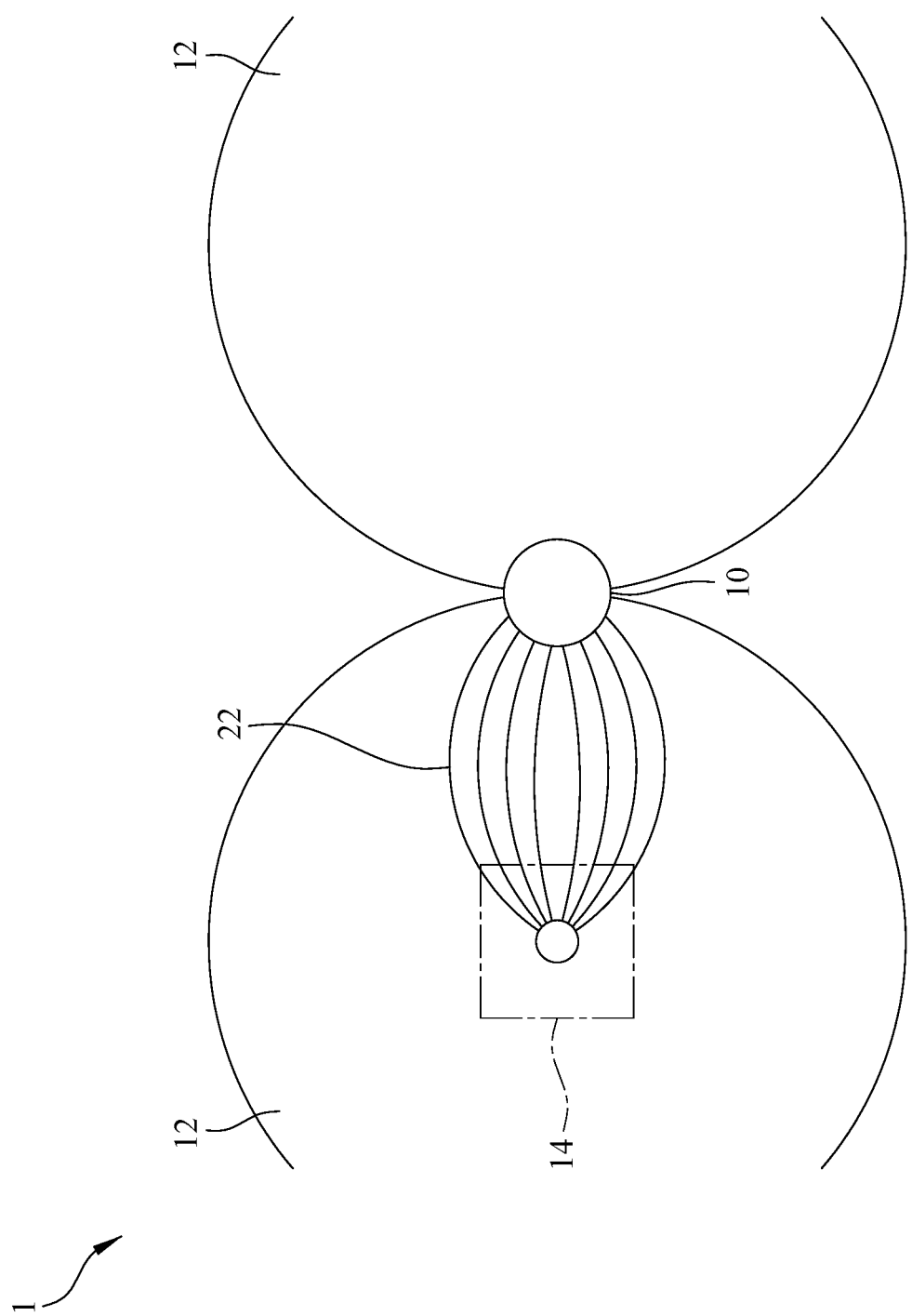
FIG. 3a is a front view illustrating a structure of an ocular fundus of a human eye.
Figure 3B:
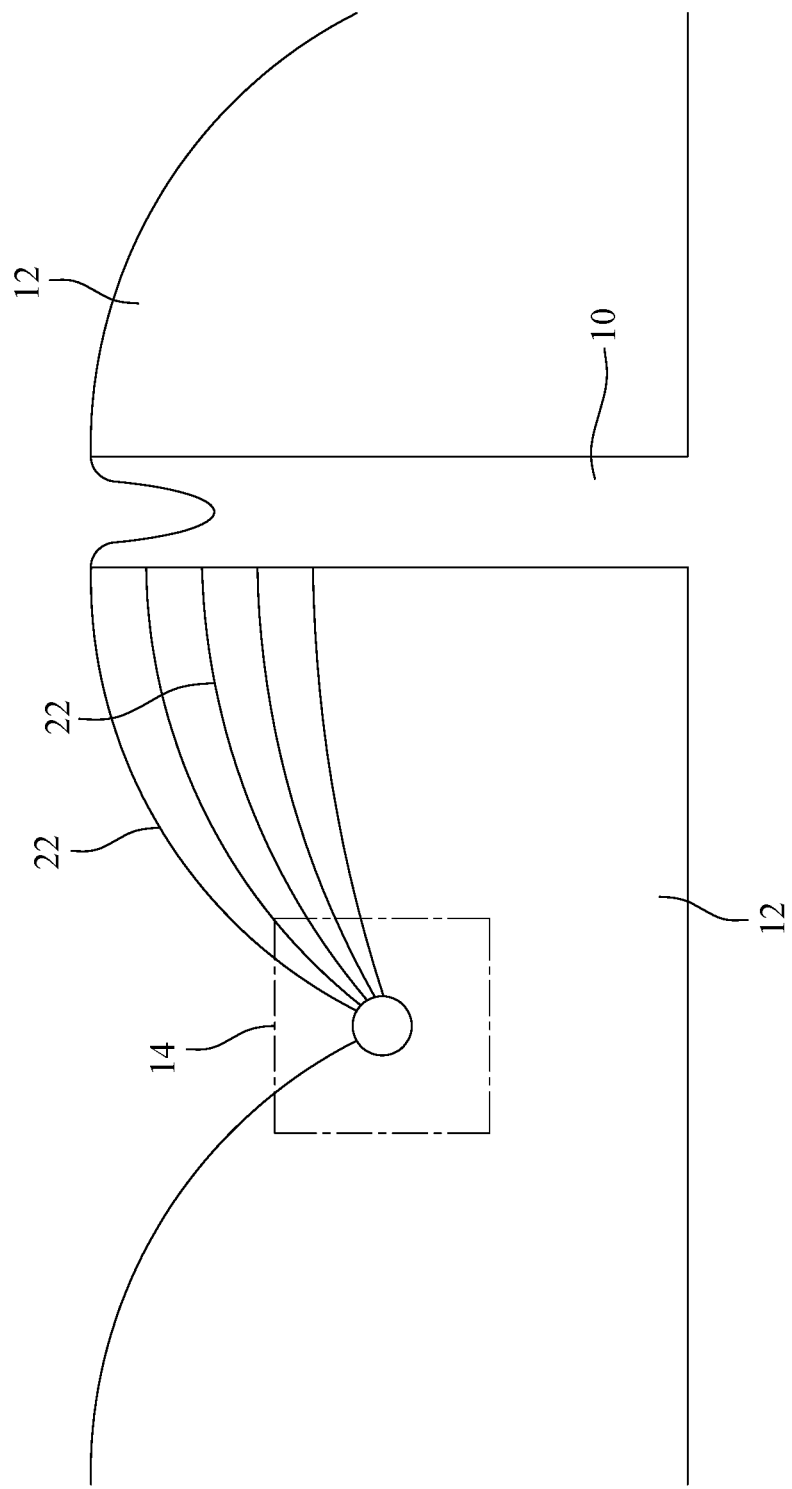
FIG. 3b is a section view illustrating the structure of the ocular fundus.

FIG. 3a is a front view illustrating a structure of an ocular fundus of a human eye. FIG. 3b is a section view illustrating the structure of the ocular fundus. FIG. 3a is a view viewed from the x-direction (i.e. the front side of the ocular fundus inside the human eye 1) indicated in FIG. 1. As shown in FIGS. 3a and 3b, the ocular fundus of the human eye 1 includes an optic nerve 10 and a retina 12. The retina 12 is filled with optic nerve fibers 22, and the optic nerve 10 and retina 12 are connected by the optic nerve fibers 22 in a macular area 14 therebetween. The optic nerve 10 collects the optic nerve fibers 22. The optic nerve fibers 22 are configured to transmit signals, and are considered as an important part of the human eye 1. The macular area 14 is located at the center of the retina 12. The center of the macular area 14 is a recessed portion, which is also known as the central fovea. It should be noted that the human eye 1 shown in FIG. 3a is a right eye. Notably, optic nerve fibers 22 are distributed on the retina 12. Only the important parts of the optic nerve fibers 22 are shown in FIGS. 3a and 3b, that is, the optic nerve fibers connecting the macular area 14 between the optic nerve 10 and the retina 12.

As shown in FIG. 3b, the optic nerve fibers connect the optic nerve 10 and the macular area 14 in a form of layers; in other words, the optic nerve fibers 22 in the retina 12 have different depths. The present invention is a new type of device for stimulating optic nerve fibers specifically designed for the optic nerve fibers 22.

Figure 4A:
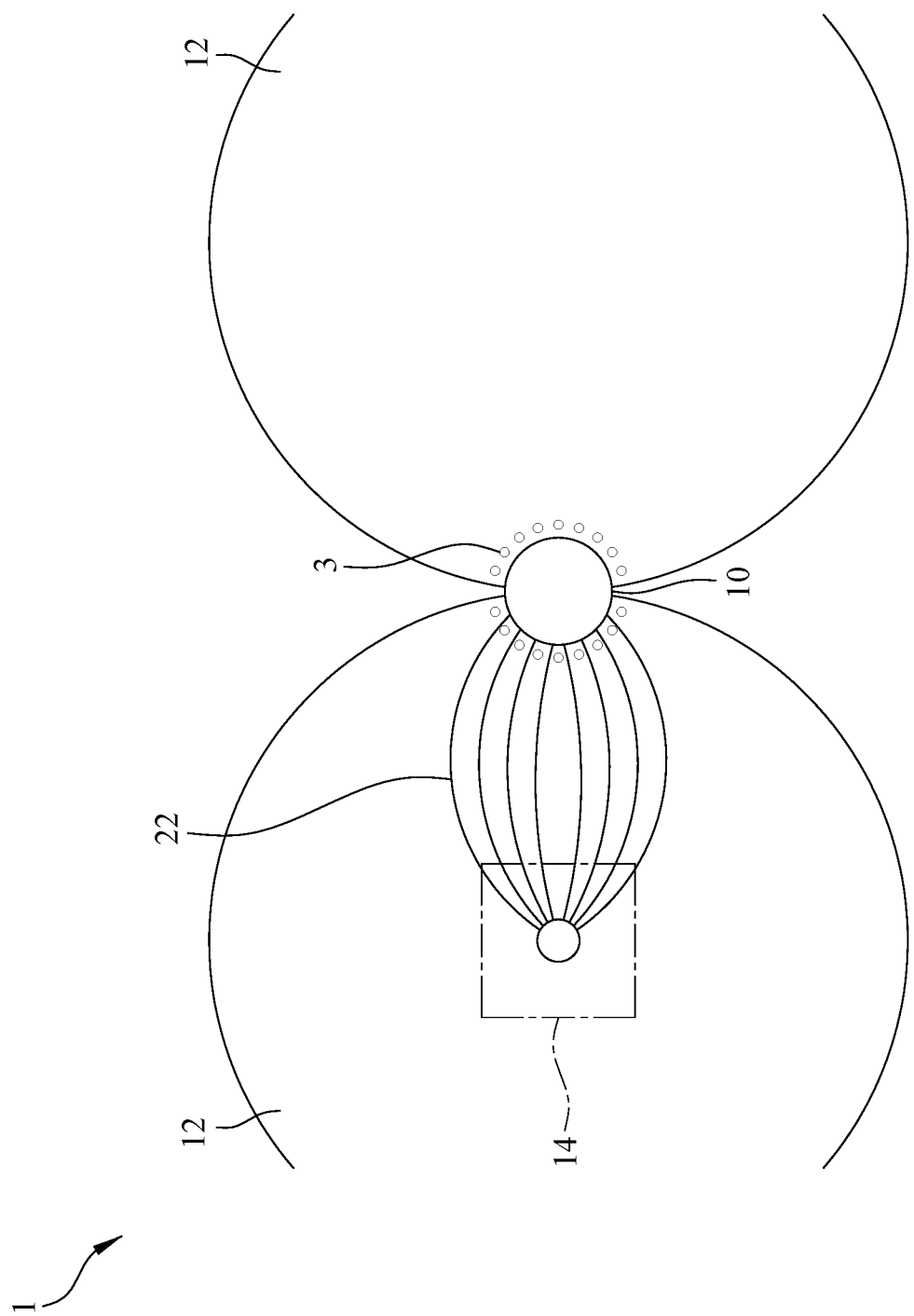
FIG. 4a is a front view illustrating a device for stimulating optic nerve fibers according to a first embodiment of the present invention, wherein the device is planted inside a human eye.
Figure 4B:
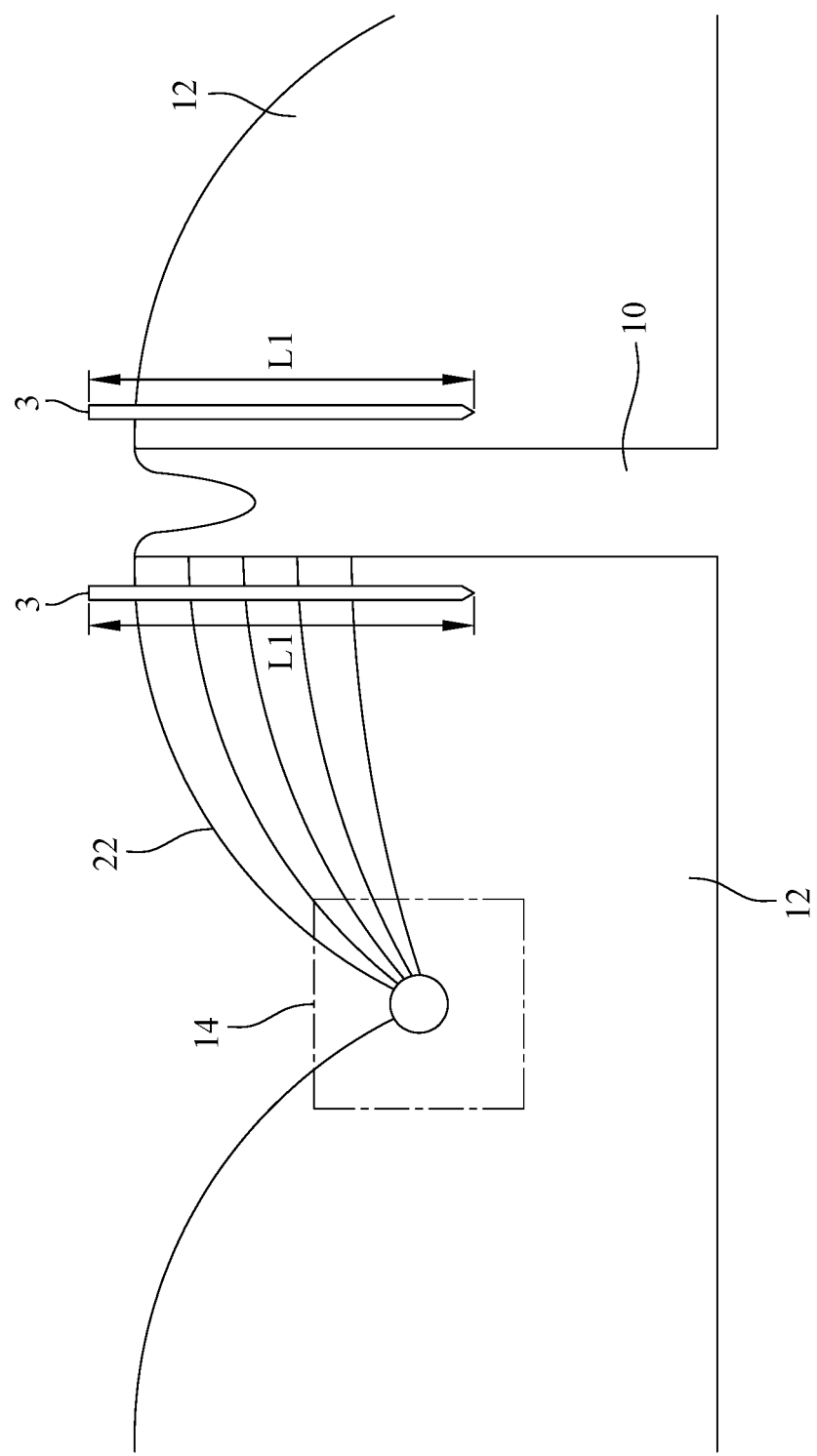
FIG. 4b is a section view illustrating the device for stimulating optic nerve fibers according to the first embodiment of the present invention, wherein the device is planted inside the human eye.

FIG. 4a is a front view illustrating a device for stimulating optic nerve fibers according to a first embodiment of the present invention. FIG. 4b is a section view illustrating the device for stimulating optic nerve fibers according to the first embodiment of the present invention. In FIGS. 4a and 4b, the device is planted inside a human eye. As shown in FIGS. 4a and 4b, in the first embodiment of the present invention, a plurality of columnar electrodes 3 are respectively disposed in parallel to a length direction of the optic nerve 10, and are also disposed around the optic nerve 10 along a circumferential direction thereof. Each of the columnar electrodes 3 has a length L1. The columnar electrodes 3 are connected with a power source (not shown). The power source is configured to supply power to the columnar electrodes 3, thereby allowing the columnar electrodes 3 to stimulate the optic nerve fibers 22 around the optic nerve with electrical stimulation.

As can be seen in FIG. 4b, each of the columnar electrodes 3 has a spiked shape at a bottom portion thereof, so the columnar electrodes 3 may be inserted smoothly into the optic nerve 10 to be disposed around the optic nerve 10 along a circumferential direction thereof. The columnar electrodes 3 of the present invention are configured to stimulate the optic nerve fibers 22 with electrical stimulation. In such a way, the optic nerve fibers 22 that are damaged or impaired may be stimulated and thus may function properly (i.e. transmit signals) once again.

Figure 5A:
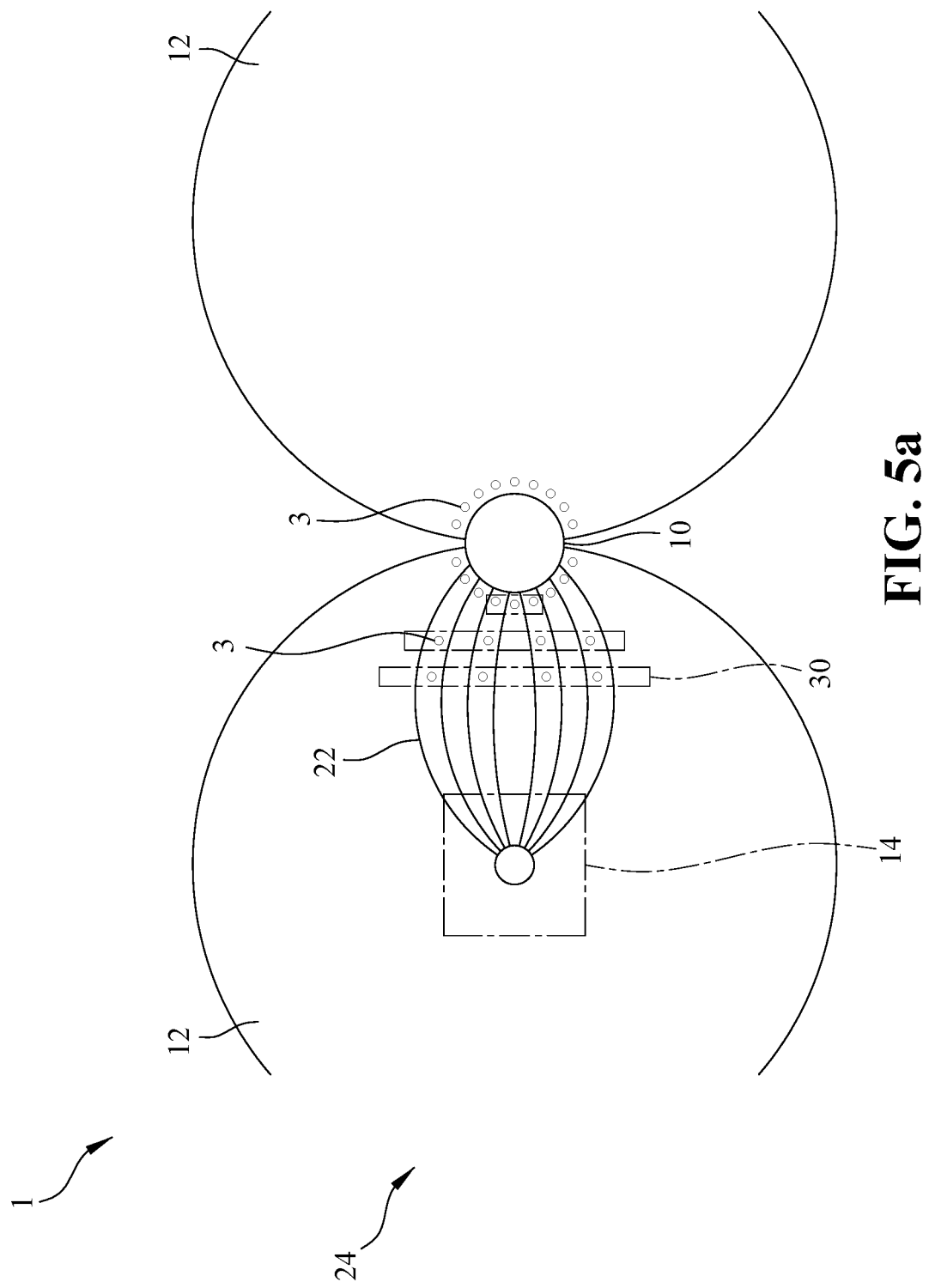
FIG. 5a is a front view illustrating a device for stimulating optic nerve fibers according to a second embodiment of the present invention, wherein the device is planted inside a human eye.

FIG. 5a is a front view illustrating a device for stimulating optic nerve fibers according to a second embodiment of the present invention, wherein the device is planted inside a human eye. As shown in FIG. 5a, in the second embodiment of the present invention, in addition to disposing the columnar electrodes 3 around the optic nerves 10, the columnar electrodes 3 are further arranged in multiple rows (in an area 30 shown in FIG. 5a) to form a rectangular array between the optic nerve 10 and the macular area 14, that is, in the direction of the human eye 1 (the right eye) that is near a side 24 of the right ear. In such a way, the stimulation area of the columnar electrodes 3 may be increased, so as to stimulate more optic nerve fibers 22. Herein, the columnar electrodes 3 in the area 30 are arranged in a same straight line.

Figure 5B:
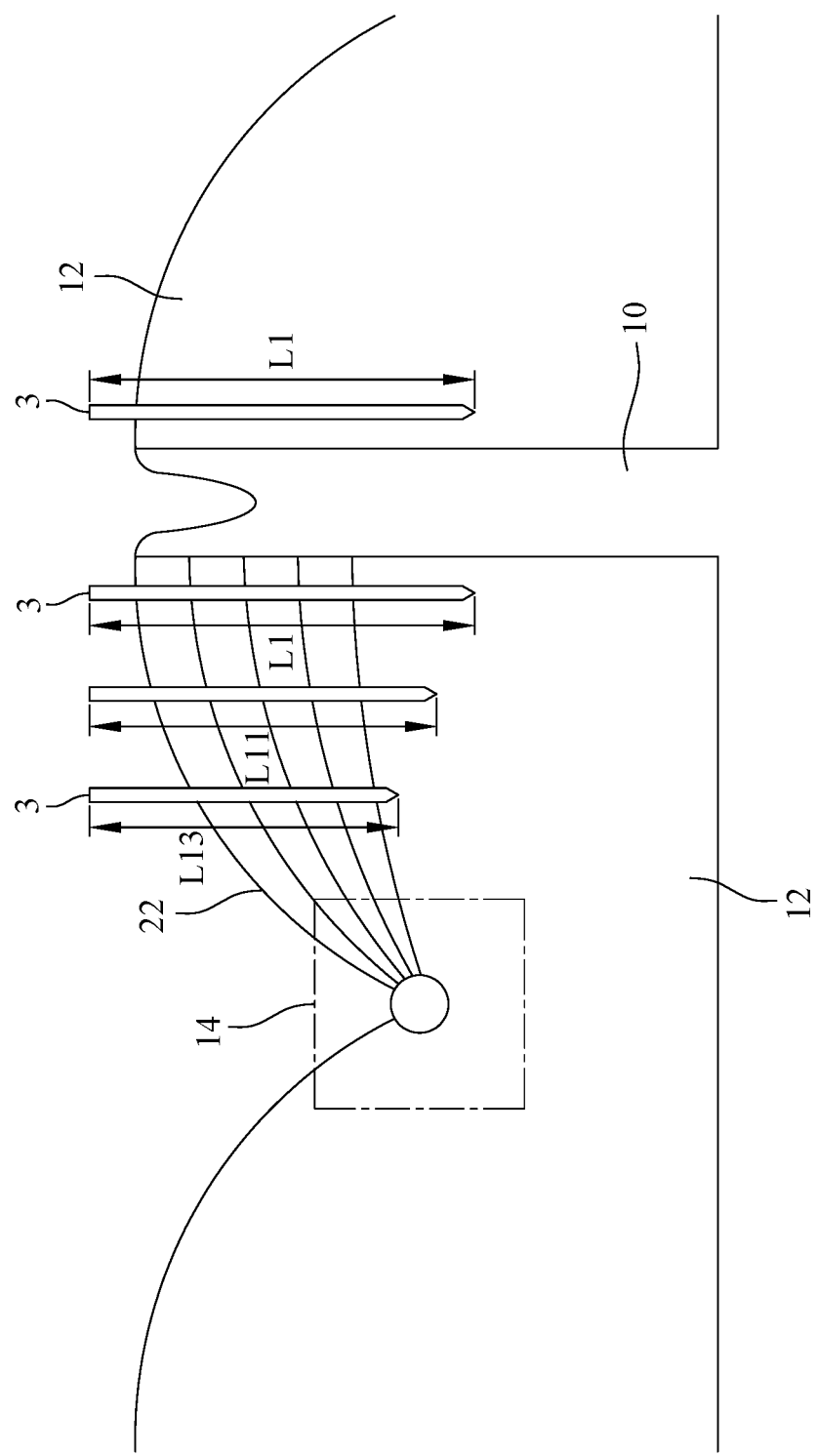
FIG. 5b is a section view illustrating the device for stimulating optic nerve fibers according to the second embodiment of the present invention, wherein the device is planted inside the human eye.

FIG. 5b is a section view illustrating the device for stimulating optic nerve fibers according to the second embodiment of the present invention, wherein the device is planted inside the human eye. As shown in FIG. 5b, it can be seen that the columnar electrodes 3 arranged in the rectangular array each has a different length. For example, the columnar electrode 3 closest to the optic nerve 10 has a length L1, the columnar electrode 3 in the middle has a length L11, and the columnar electrode 3 on the left side has a length L13. Herein, the length L1 is greater than L11, and the length L11 is greater than L13. In the second embodiment of the present invention, columnar electrodes 3 with different lengths may be chosen based on a curvature of the optic nerve fibers 22, so the columnar electrodes 3 may stimulate the optic nerve fibers 22 with electrical stimulation in a more efficient way. It should be understood that columnar electrodes 3 with the same lengths may also be used in other embodiments of the present invention.

Figure 5C:
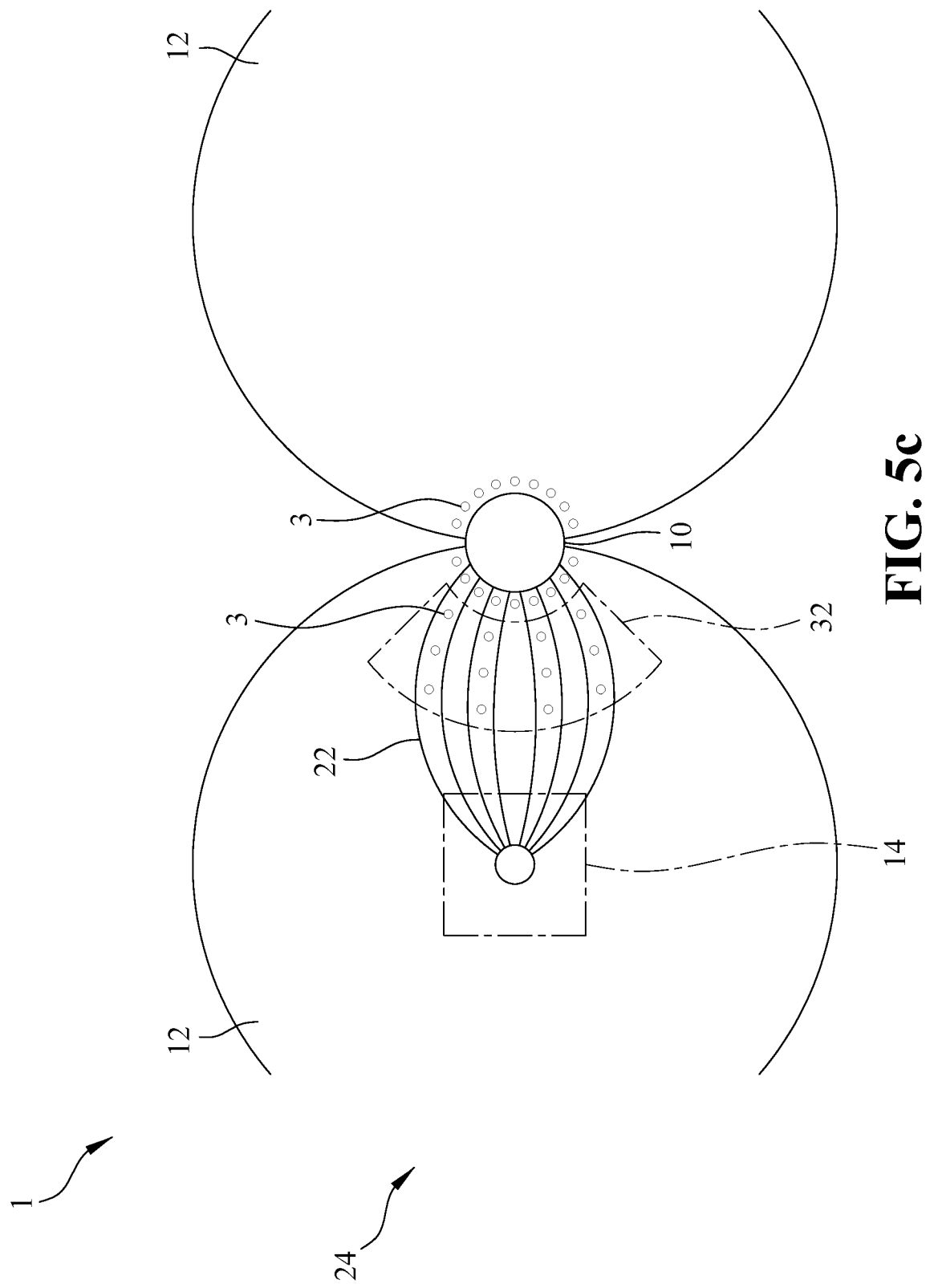
FIG. 5c is a front view illustrating a device for stimulating optic nerve fibers according to a third embodiment of the present invention, wherein the device is planted inside a human eye.

FIG. 5c is a front view illustrating a device for stimulating optic nerve fibers according to a third embodiment of the present invention, wherein the device is planted inside a human eye. As shown in FIG. 5c, the columnar electrodes are further arranged in a fan-shaped array 32. The columnar electrodes 3 arranged in the fan-shaped array 32 may further increase the stimulation area thereof, thereby stimulating optic nerve fibers 22 in more numbers and stimulating fibers that are further away (away from the macular area 14). Herein, columnar electrodes 3 in the fan-shaped array 32 do not form the area 30 as shown in FIG. 5a (i.e. electrodes are not arranged on a same straight line). In addition, it should be noted that columnar electrodes 3 with different lengths may also be chosen based on the curvatures of optic nerve fibers 22 in the third embodiment.

Figure 6A:
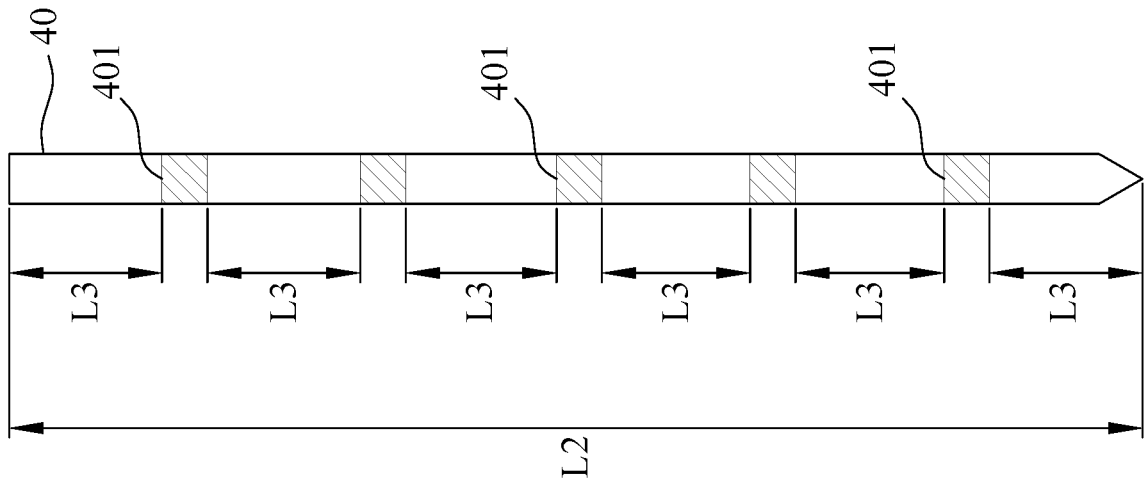
FIG. 6a is a schematic view illustrating a device for stimulating optic nerve fibers according to a fourth embodiment of the present invention.

FIG. 6a is a schematic view illustrating a device for stimulating optic nerve fibers according to a fourth embodiment of the present invention. As shown in FIG. 6a, a plurality of lateral electrodes 401 is disposed on each of the columnar electrodes 40 in the fourth embodiment of the present invention, thereby forming an improved columnar electrode 4. Herein, each of the lateral electrodes 401 may function independently to perform electrical stimulation. Further, the lateral electrodes 401 may be evenly distributed on the columnar electrodes 40 based on a length L2 of the columnar electrode 40. For example, the lateral electrodes 401 may be disposed on the columnar electrodes 40 with a spacing L3 between each of the lateral electrodes 401.

In the fourth embodiment of the present invention, the lateral electrodes 401 may be disposed on each columnar electrode 40 in various ways. FIG. 6b is a section view illustrating a first structure of the device for stimulating optic nerve fibers according to the fourth embodiment of the present invention. In FIG. 6b, a first structure of the lateral electrodes 401 is shown. In the first structure, each of the columnar electrodes 40 has a plurality of recessed portions 42, and each of the recessed portions 42 has an insulation layer 44. The lateral electrodes 401 may be embedded into the recessed portions 42 having the insulation layers 44, so the lateral electrodes 401 are separated from the columnar electrodes 40 by the insulation layers 44. Herein, each of the columnar electrodes 40 is connected with a wire 4011, and the wire 4011 is connected to a power source (not shown). The wire 4011 may further penetrate through recessed portions 42 and insulation layers 44 to be connected to the lateral electrodes 401. In such a way, each of the lateral electrodes 401 may function independently in terms of electrical stimulation.

Figure 6C:
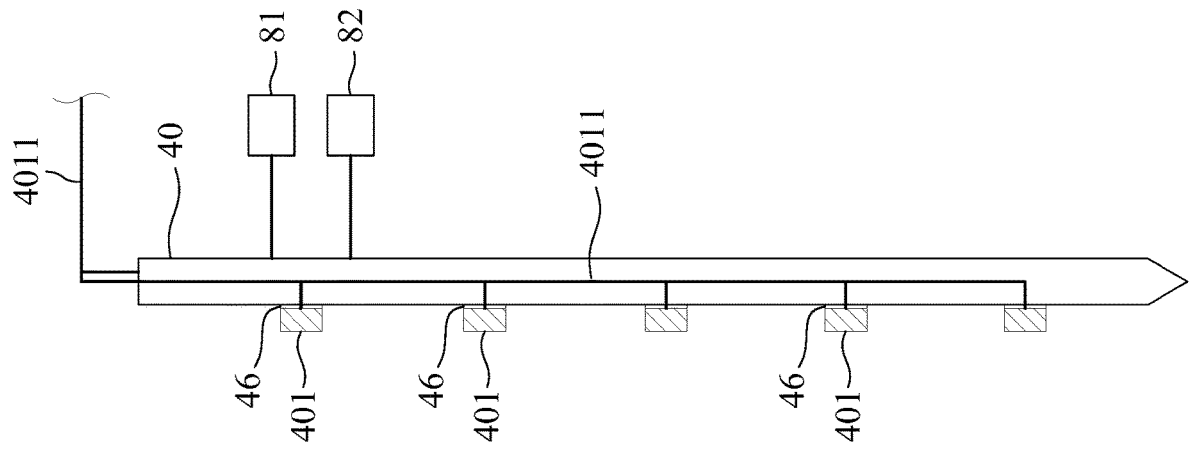
FIG. 6c is a section view illustrating a second structure of the device for stimulating optic nerve fibers according to the fourth embodiment of the present invention.
Figure 6B:
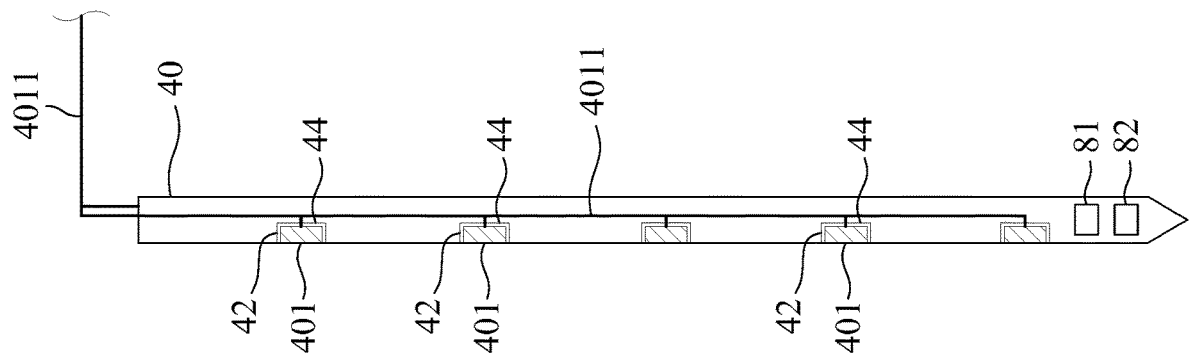
FIG. 6b is a section view illustrating a first structure of the device for stimulating optic nerve fibers according to the fourth embodiment of the present invention.

FIG. 6c is a section view illustrating a second structure of the device for stimulating optic nerve fibers according to the fourth embodiment of the present invention. In FIG. 6c, a second structure of the lateral electrodes 401 is shown. In the second structure, each of the lateral electrodes 401 is attached to an insulation layer 46, and the insulation layers 46 attached with lateral electrodes 401 are attached to columnar electrodes 40, thereby separating each of the lateral electrodes 401 from the columnar electrode 40. Herein, each of the columnar electrodes 40 is connected with a wire 4011, and the wire 4011 is connected to a power source (not shown). The wire 4011 may further penetrate through columnar electrodes 40 and insulation layers 46 to be connected to the lateral electrodes 401. In such a way, each of the lateral electrodes 401 may function independently in terms of electrical stimulation.

It should be understood that for the simplicity of illustration, the lateral electrodes 401 is protruding from the columnar electrodes 40 in the state shown in FIG. 6c; however, the lateral electrodes 401 do not necessarily protrude from the columnar electrodes 40 in such a way. In an embodiment of the present invention, the lateral electrodes 401 may be implemented as electrode patches with a very small thickness. Thus, the thickness of the lateral electrodes 401 may be neglected, and the columnar electrodes attached with the lateral electrodes 401 may be inserted smoothly into the periphery of the optic nerve.

Figure 6D:
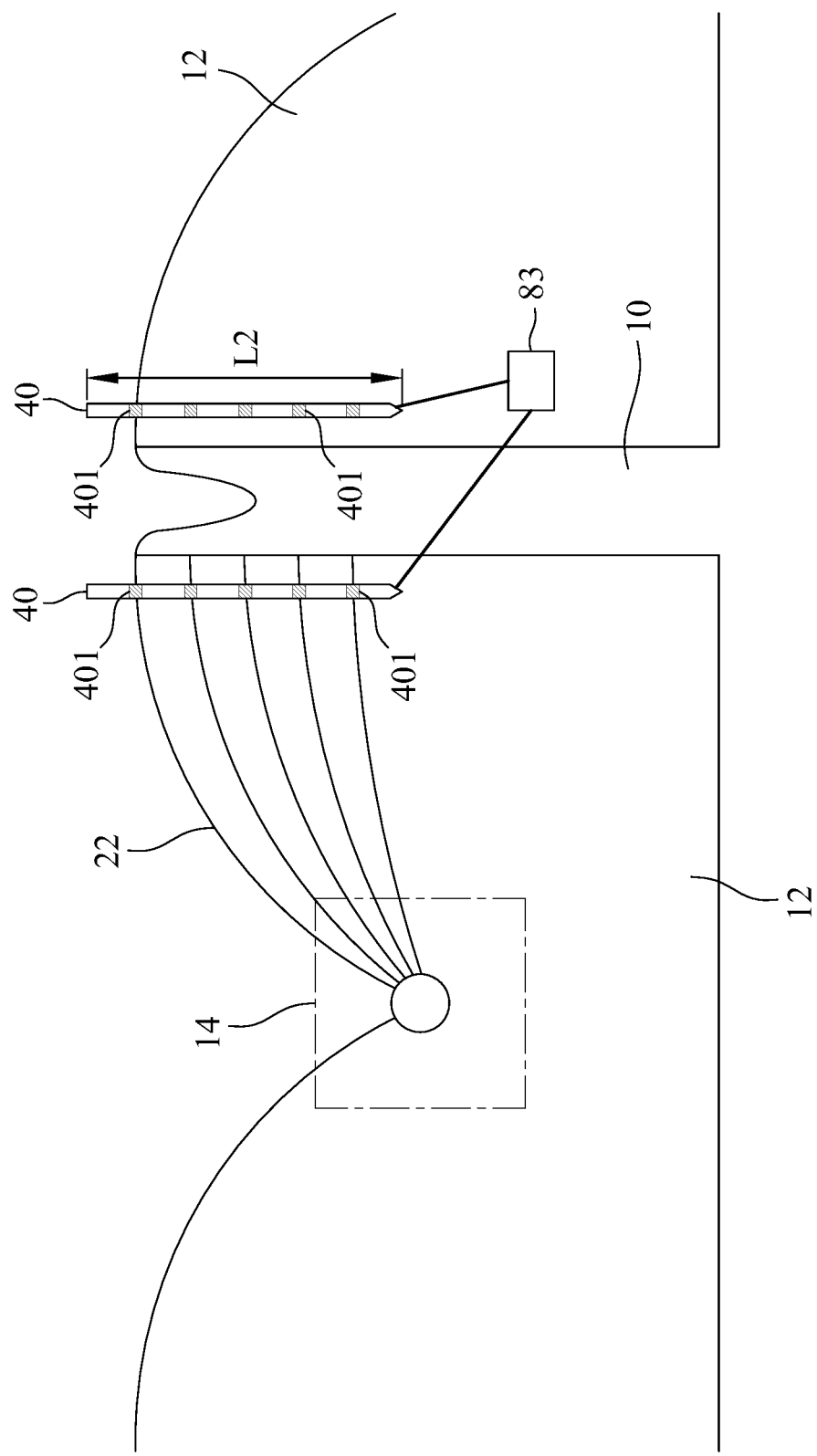
FIG. 6d is a section view illustrating the device for stimulating optic nerve fibers according to the fourth embodiment of the present invention being planted inside a human eye.

FIG. 6d is a section view illustrating the device for stimulating optic nerve fibers according to the fourth embodiment of the present invention being planted inside a human eye. Herein, the columnar electrodes 40 in FIG. 6d are simplified structures of the electrodes shown in FIG. 6a. It should be understood that the columnar electrodes 40 in FIG. 6d may also be replaced by the structures shown in FIG. 6b or 6c. As shown in FIG. 6d, in the fourth embodiment of the present invention, when each of the columnar electrodes is provided with multiple lateral electrodes 401, each of the lateral electrodes 401 is capable of providing electrical stimulation in an independent manner. In other words, as compared to the columnar electrodes 3 provided without the lateral electrodes shown in FIG. 4b, the columnar electrodes 40 including the lateral electrodes 401 allow each of the lateral electrodes to perform electrical stimulation independently, thereby enhancing the stimulation to different layers of the optic nerve fibers 22 amongst the multiple layers of the optic nerve fibers 22 (i.e. stimulate optic nerve fibers 22 at different depths). In such a way, optic nerve fibers 22 may be stimulated in a stronger and more effective way, thus allowing damaged or impaired optic nerve fibers 22 to function properly.

It should be noted that the improved columnar electrodes 4 may be disposed between the optic nerve 10 and the macular area 14 such that the columnar electrodes 40 are arranged in multiple rows to form an array. Examples of such an array may include the rectangular array and the fan-shaped array shown in FIG. 5a and FIG. 5c, respectively.

Figure 6E:
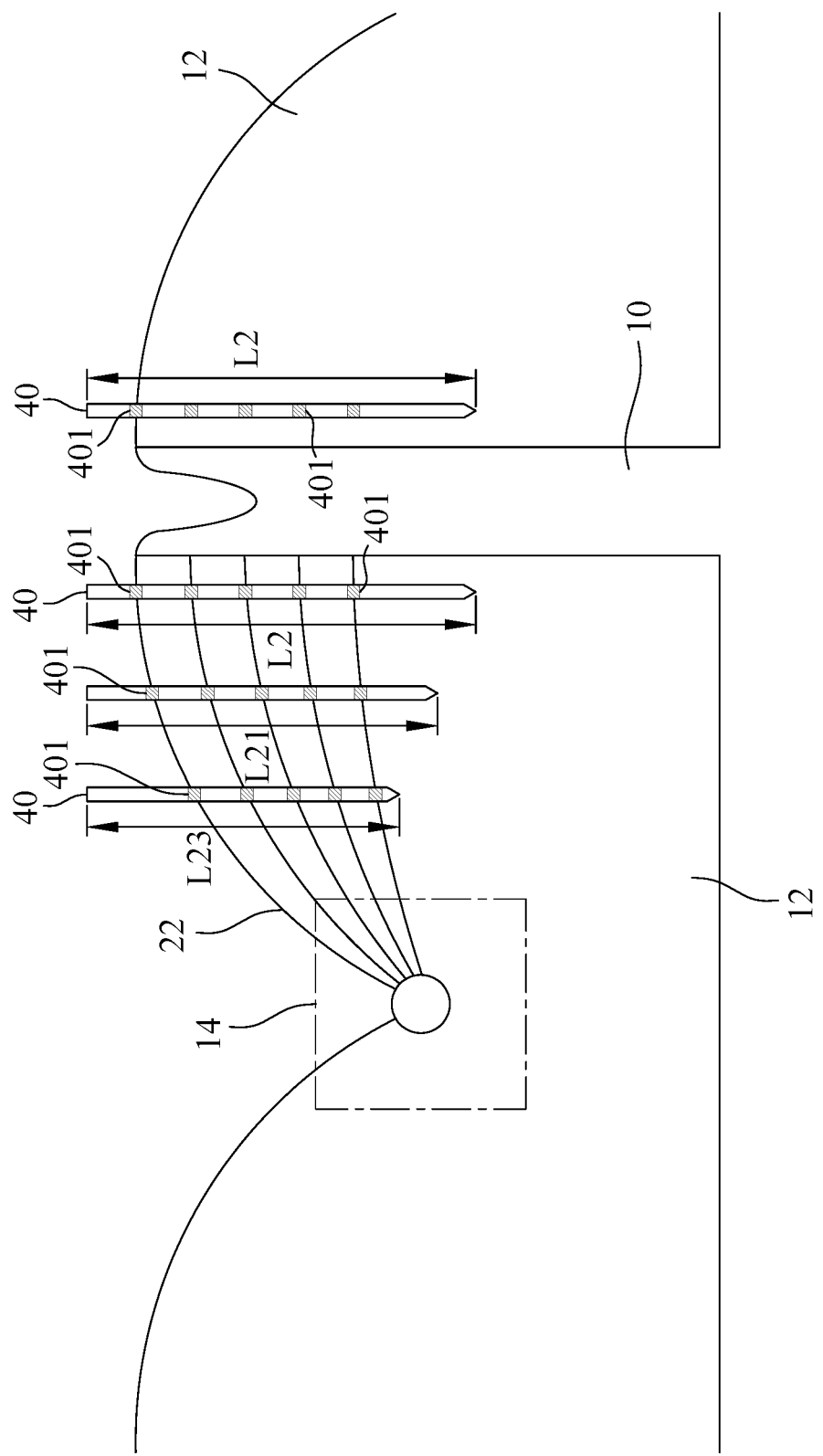
FIG. 6e is a section view illustrating a device for stimulating optic nerve fibers according to a fifth embodiment of the present invention being planted inside a human eye.

FIG. 6e is a section view illustrating a device for stimulating optic nerve fibers according to a fifth embodiment of the present invention being planted inside a human eye. FIG. 6e is to illustrate the columnar electrodes 40 being planted inside the human eye while arranged in a rectangular array or a fan-shaped array. As shown in FIG. 6e, the columnar electrodes 40 arranged in arrays may have different lengths from each other. For example, the columnar electrode 40 closest to the optic nerve 10 has a length L2, the columnar electrode 40 in the middle has a length L21, and the columnar electrode 40 on the left side has a length L23. In the fifth embodiment of the present invention, columnar electrodes 40 with different lengths may be chosen based on a curvature of the optic nerve fibers 22, so the columnar electrodes 40 may stimulate the optic nerve fibers 22 with electrical stimulation in a more efficient way. It should be understood that columnar electrodes 40 with the same lengths may also be used in other embodiments of the present invention.

Furthermore, once the columnar electrodes 40 are arranged in a rectangular array or a fan-shaped array, each of the columnar electrodes 40 is also provided with a plurality of lateral electrodes 401. Each of the lateral electrodes 401 is configured to perform electrical stimulation independently, thereby enhancing the stimulation of different layers of the optic nerve fibers 22 amongst the multiple layers of the optic nerve fibers 22 (i.e. stimulate optic nerve fibers 22 at different depths). In such a way, optic nerve fibers 22 may be stimulated in a stronger and more effective way, thus allowing damaged or impaired optic nerve fibers 22 to function properly.

On the other hand, in other embodiments of the present invention, various configurations may be used to control the columnar electrodes 3 or the columnar electrodes 40 described above (whether to perform electrical stimulation). Hereafter, a first control configuration will be described. In the first control configuration, a sensor 81 and a controller 82, which are disposed inside the human eye, are electrically connected to the columnar electrodes 3 or the columnar electrodes 40 as shown in FIG. 6c. When light from an external light source enters the sensor 81 (i.e. when light from an external light incident into the human eye, a visual signal is acquired), a signal is sent to the controller 82 from the sensor 81, thereby controlling the columnar electrodes 3 or the columnar electrodes 40 to perform electrical stimulation.

In a second control configuration, a sensor 81 and a controller 82, which are electrically connected with each other, are further disposed on each of the columnar electrodes 3 or the columnar electrodes 40 as shown in FIG. 6b. The sensor 81 is configured to detect whether an optical signal has been transmitted to the optic nerve 10. When the sensor 81 detects that the optic signal has been transmitted to the optic nerve 10, a signal is sent to the controller 82 from the sensor 81, thereby controlling the columnar electrodes 3 or the columnar electrodes 40 to perform electrical stimulation.

In a third control configuration, a photo-electrical convertor 83, which is electrically connected to the columnar electrodes 3 or the columnar electrodes 40 as shown in FIG. 6d, is further disposed in the human eye. When light from an external light source enters the human eye, the photo-electrical convertor 83 is configured to convert light energy of the external light into electrical energy, and further configured to supply the electrical energy to the columnar electrodes 3 or the columnar electrodes 40. That is, in the third control configuration, the columnar electrodes 3 or the columnar electrodes 40 are controlled by photo-electrical conversion so as to perform electrical stimulation.

Figure 7A:
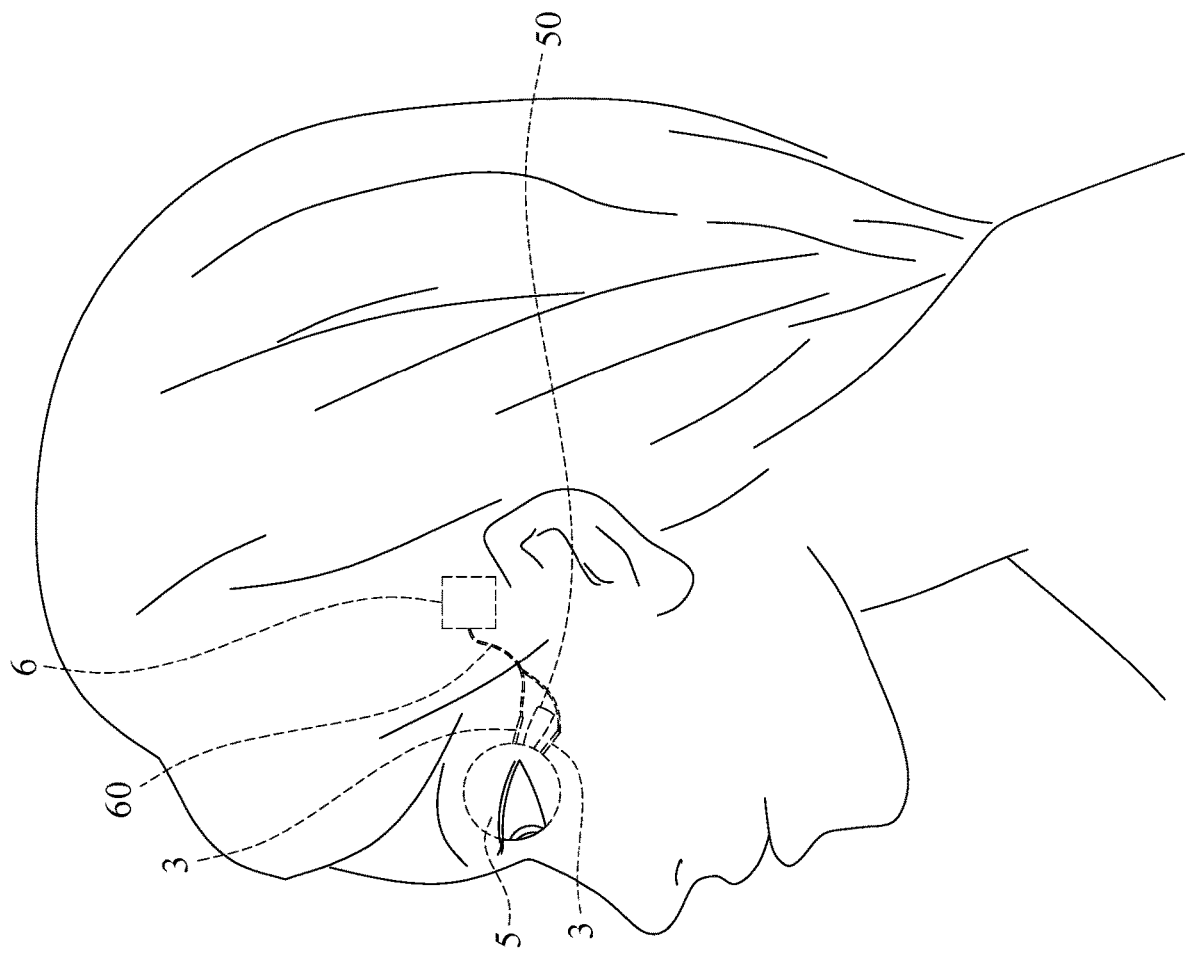
FIG. 7a is a schematic view illustrating one implementation of a power source of the present invention.

FIG. 7a is a schematic view illustrating one implementation of a power source of the present invention. As shown in FIG. 7a, in one embodiment of the present invention, when the columnar electrodes 3 are disposed around the optic nerve 50 of a left eye 5, the plurality of columnar electrodes 3 (or, the columnar electrodes 40, not shown in FIG. 7a) may be connected to a power source 6 via a wire 60. The wire 60 may be embedded in a human body. The power source 6 may be disposed inside or outside of the human body based on choice. Moreover, in other embodiments of the present invention, a power source 6 may be directly disposed inside each of the columnar electrodes 3 (or columnar electrodes 40, not shown in FIG. 7a). FIG. 7c illustrates an implementation in which a power source 8 is disposed inside each of the columnar electrodes 3.

Figure 7B:
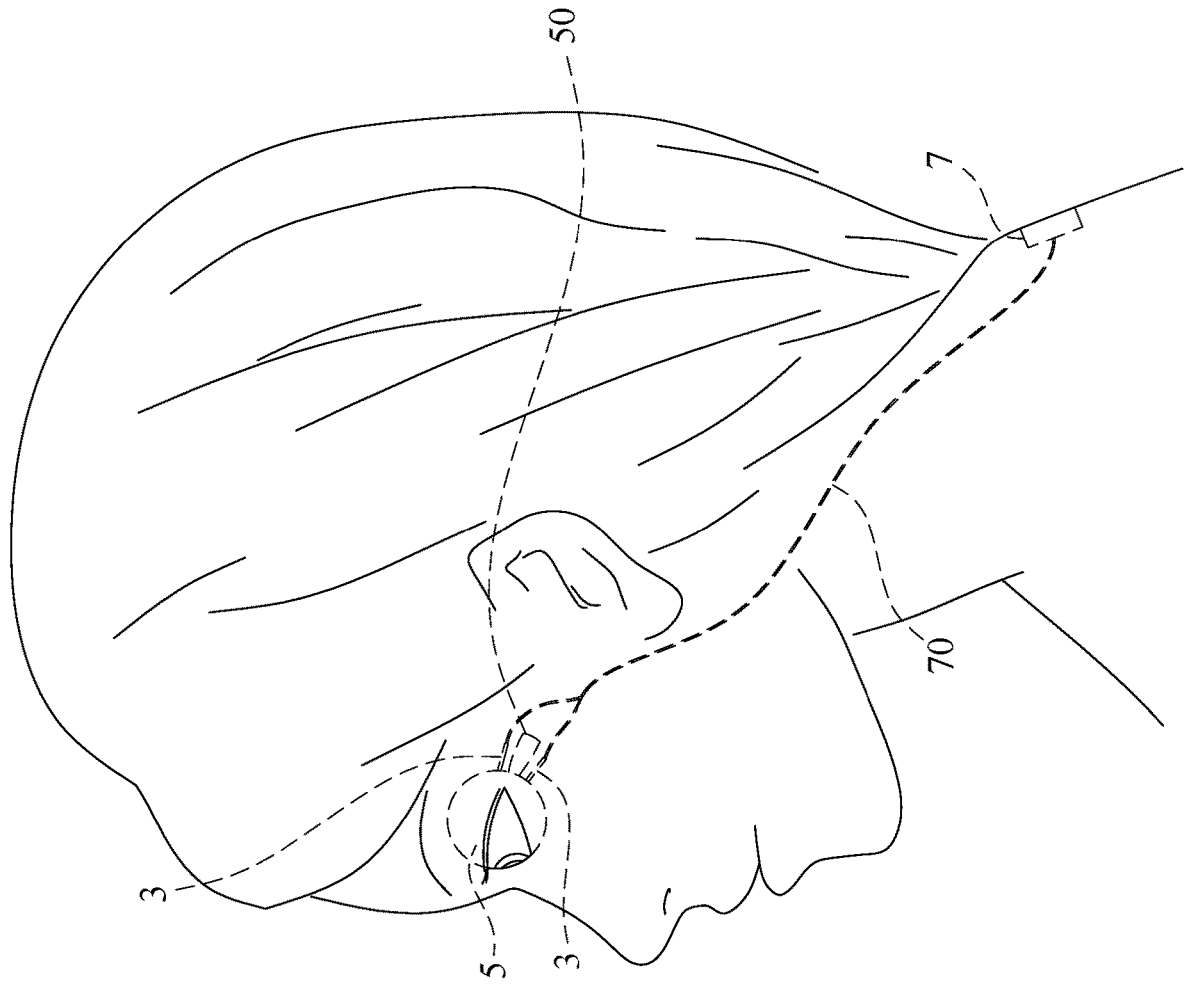
FIG. 7b is a schematic view illustrating another implementation of the power source of the present invention.
Figure 7C:
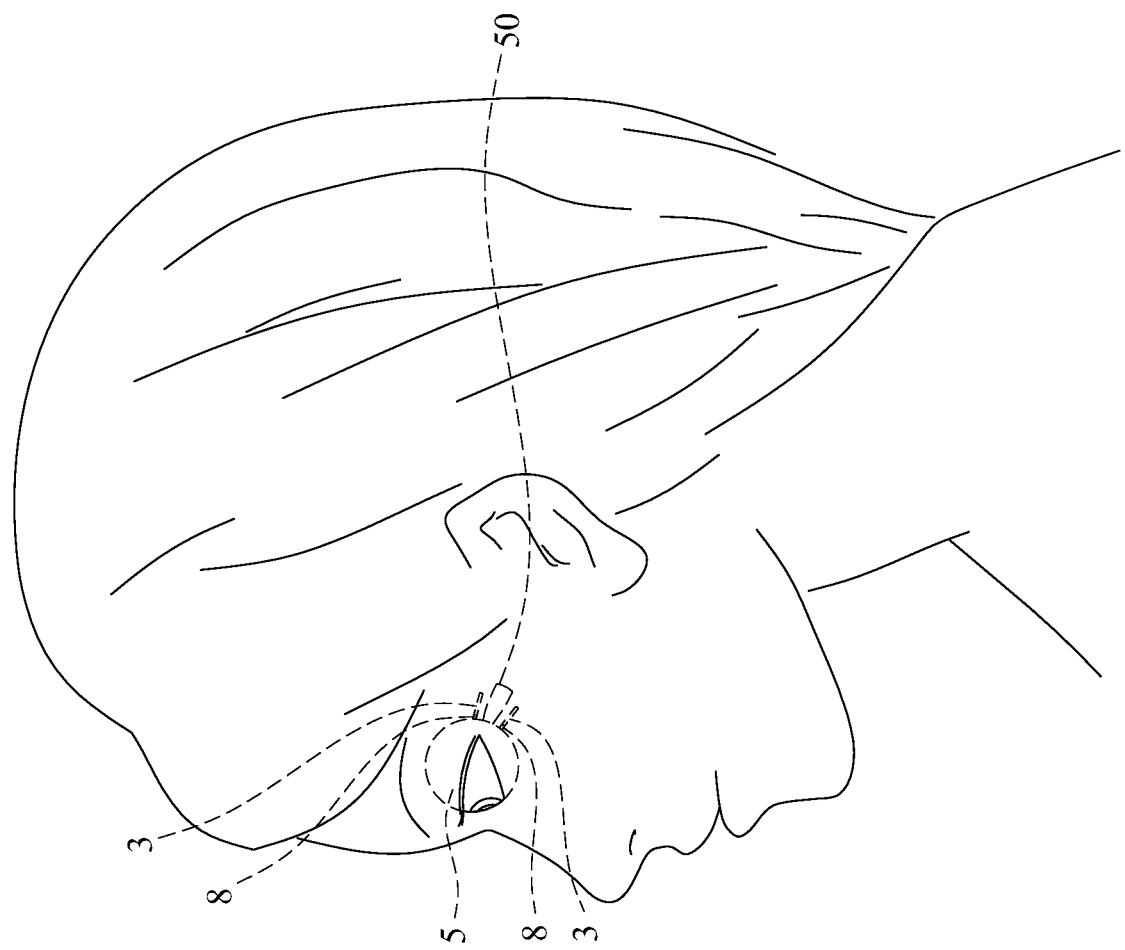
FIG. 7c is a schematic view illustrating an implementation in which a power source is disposed inside each of the columnar electrodes.

FIG. 7b is a schematic view illustrating another implementation of the power source of the present invention. As shown in FIG. 7b, in another embodiment of the present invention, when the columnar electrodes 3 are disposed around the optic nerve 50 of a left eye 5, the plurality of columnar electrodes 3 (or, the columnar electrodes 40, not shown in FIG. 7b) may be connected to a power source 7 via a wire 70. The wire 70 may be embedded in a human body. The power source 7 shown in FIG. 7b may be a solar powered power source that is embedded under the skin of the human body near the back of the neck; however, the embedding position is not limited thereto). In such a way, when the user is under any light sources (e.g. sunlight, electric lamps, etc.), the power source 7 may generate electricity from the light energy and further supply the electricity to the columnar electrodes 3 (columnar electrodes 40, not shown in FIG. 7b).

From the above description, it can be learned that the present invention has successfully provided a new device for stimulating optic nerve fibers. The columnar electrode provided by the present invention has a simple structure, and is capable of effectively stimulating the optic nerve fibers. When the columnar electrodes are further arranged in arrays, or when the columnar electrodes are provided with lateral electrodes, the stimulation area of the columnar electrodes may be further increased, and the stimulation effect thereof may also be enhanced. Further, the columnar electrodes of the present invention can be simply inserted into the periphery of the optic nerve, which are very easy to install. Moreover, the columnar electrodes of the present invention are not in touch with the optic nerve, thereby lowering the danger in implementation.

Although the operation of the method according to the embodiments of the present invention has been described in a certain order, it is not meant to limit the order of the steps. It should be apparent to those skilled in the art that the method can also be performed in a different order. Therefore, the order of the steps should not be seen as a limitation to the claims of the present invention. In addition, the method in the claims should not be limited by the order of steps described above. Those who are skilled in the art should understand that the order of the steps can be changed without departing from the scope of the present invention.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A method for stimulating optic nerve fibers of an optic nerve of a human eye, comprising the steps of:
   preparing a plurality of columnar electrodes and planting the plurality of columnar electrodes into the optic nerve fibers that connect the optic nerve to a macular area in a retina of the human eye, the columnar electrodes being arranged circularly around the optic nerve with each of the columnar electrodes having an elongated direction in parallel with an elongated direction of the optic nerve;
   configuring a power source to supply power to the plurality of columnar electrodes; and
   stimulating the optic nerve fibers by electrical stimulation using the plurality of columnar electrodes.

2. The method according to claim 1, wherein the columnar electrodes are further connected electrically to a sensor and a controller, which are adapted to be located inside the human eye, and when light from an external light source enters the sensor, a signal is sent to the controller from the sensor, thereby controlling the columnar electrodes to perform electrical stimulation via the controller.

3. The method according to claim 1, wherein each of the columnar electrodes is further disposed with a sensor and a controller, which are electrically connected with each other, and when light from an external light source enters the sensor, a signal is sent to the controller from the sensor, thereby controlling the columnar electrodes to perform electrical stimulation via the controller.

4. The method according to claim 1, wherein the columnar electrodes are further connected electrically to a photo-electrical convertor adapted to be located in the human eye and when light from an external light source enters the human eye, the photo-electrical convertor converts light energy of the light into electrical energy and further supplies the electrical energy to the columnar electrodes, thereby allowing the columnar electrodes to perform electrical stimulation.

5. The method according to claim 1, wherein the power source is disposed inside each of the columnar electrodes, or adapted to be located inside or outside the human body.

6. The method according to claim 1, wherein the power source is a solar powered power source.

7. The method according to claim 1, wherein each of the columnar electrodes comprises a plurality of lateral electrodes disposed thereon along the elongated direction, and each of the lateral electrodes is configured for stimulating a different layer of the optic nerve fibers amongst multiple layers of the optic nerve fibers by electrical stimulation.

8. The method according to claim 7, wherein the lateral electrodes are evenly distributed in the elongated direction on each of the columnar electrodes.

9. The method according to claim 7, wherein each of the columnar electrodes comprises a plurality of recessed portions, each of the recessed portions comprises an insulation layer, and each of the lateral electrodes is embedded into each of the recessed portions having the insulation layer.

10. The method according to claim 7, wherein each of the columnar electrodes has a plurality of insulation members disposed thereon along the elongated direction, and each of the lateral electrodes corresponds to one of the insulation members and is attached to a corresponding insulation member.

11. The method according to claim 1, further comprising the steps of:
    preparing a plurality of additional columnar electrodes and planting the additional columnar electrodes into the optic nerve fibers between the macular area and the optic nerve, each of the additional columnar electrodes having an elongated direction in parallel with the elongated direction of the optic nerve;
    configuring the power source to supply power to the plurality of additional columnar electrodes; and
    stimulating the optic nerve fibers by electrical stimulation using the plurality of additional columnar electrodes;
    wherein the additional columnar electrodes are arranged as a rectangular array or a fan-shaped array and disposed between the macular area and the optic nerve.

12. The method according to claim 11, wherein the columnar electrodes and the additional columnar electrodes are further connected electrically to a sensor and a controller, which are adapted to be located inside the human eye, and when light from an external light source enters the sensor, a signal is sent to the controller from the sensor, thereby controlling the columnar electrodes and the additional columnar electrodes to perform electrical stimulation via the controller.

13. The method according to claim 11, wherein each of the columnar electrodes and the additional columnar electrodes is further disposed with a sensor and a controller, which are electrically connected with each other, and when light from an external light source enters the sensor, a signal is sent to the controller from the sensor, thereby controlling the columnar electrodes and the additional columnar electrodes to perform electrical stimulation via the controller.

14. The method according to claim 11, wherein the columnar electrodes and the additional columnar electrodes are further connected electrically to a photo-electrical convertor adapted to be located in the human eye and when light from an external light source enters the human eye, the photo-electrical convertor converts light energy of the light into electrical energy and further supplies the electrical energy to the columnar electrodes and the additional columnar electrodes, thereby allowing the columnar electrodes and the additional columnar electrodes to perform electrical stimulation.

15. The method according to claim 11, wherein each of the columnar electrodes and the additional columnar electrodes has a length and the lengths of the columnar electrodes and the additional columnar electrodes are not all identical.

16. The method according to claim 15, each of the lengths of the columnar electrodes and the additional columnar electrodes is adjusted according to curvatures of the optic nerve fibers.

17. The method according to claim 11, wherein each of the columnar electrodes and the additional columnar electrodes comprises a plurality of lateral electrodes disposed thereon along the elongated direction, and each of the lateral electrodes is configured for stimulating a different layer of the optic nerve fibers amongst multiple layers of the optic nerve fibers by electrical stimulation.

18. The method according to claim 17, wherein the lateral electrodes are evenly distributed in the elongated direction on each of the columnar electrodes and the additional columnar electrodes.

19. The method according to claim 17, wherein each of the columnar electrodes comprises a plurality of recessed portions, each of the recessed portions comprises an insulation layer, and each of the lateral electrodes is embedded into each of the recessed portions having the insulation layer.

20. The method according to claim 17, wherein each of the columnar electrodes and the additional columnar electrodes has a plurality of insulation members disposed thereon along the elongated direction, and each of the lateral electrodes corresponds to one of the insulation members and is attached to a corresponding insulation member.

* * * * *